US009526479B2

United States Patent
Hügle et al.

(10) Patent No.: US 9,526,479 B2
(45) Date of Patent: Dec. 27, 2016

(54) ENDOSCOPIC INSTRUMENT FOR RETROGRADE BIOPSY, IN PARTICULAR SYNOVIAL BIOPSY

(71) Applicant: Karl Storz GmbH & Co. KG, Tuttlingen (DE)

(72) Inventors: Thomas Hügle, Freiburg (DE); Alexander Fuchs, Steiβlingen (DE)

(73) Assignee: KARL STORZ GMBH & CO. KG, Tuttlingen (DE)

( * ) Notice: Subject to any disclaimer, the term of this patent is extended or adjusted under 35 U.S.C. 154(b) by 366 days.

(21) Appl. No.: 14/097,664

(22) Filed: Dec. 5, 2013

(65) Prior Publication Data

US 2014/0171824 A1 Jun. 19, 2014

(30) Foreign Application Priority Data

Dec. 19, 2012 (DE) ........................ 10 2012 223 788

(51) Int. Cl.
*A61B 10/02* (2006.01)
*A61B 10/06* (2006.01)

(52) U.S. Cl.
CPC ......... *A61B 10/0266* (2013.01); *A61B 10/025* (2013.01); *A61B 10/0283* (2013.01); *A61B 10/06* (2013.01)

(58) Field of Classification Search
CPC .................................................... A61B 10/06
See application file for complete search history.

(56) References Cited

U.S. PATENT DOCUMENTS 4,054,143 A * 10/1977 Bauer ................ A61B 18/1442
606/52
5,320,110 A 6/1994 Wang
(Continued)

FOREIGN PATENT DOCUMENTS

DE 199 55 592 A1 6/2000
DE 103 48 188 A1 5/2004
(Continued)

OTHER PUBLICATIONS

Search Report from German Patent Application No. 10 2012 223 788.7, dated Jul. 1, 2013, 4 pages.
(Continued)

*Primary Examiner* — Adam J Eiseman
*Assistant Examiner* — Patrick Fernandes
(74) *Attorney, Agent, or Firm* — Rothwell, Figg, Ernst & Manbeck, P.C.

(57) ABSTRACT

The present invention relates to an endoscopic instrument for retrograde biopsy, in particular synovial biopsy, comprising a head unit (12) having a distal tip portion (36) for penetrating tissue, a jaw part (24) with a tissue engaging formation (38) for removing the biopsy specimen, the jaw part (24) being pivotable from an idle position to an operating position in the direction of the distal tip portion (36) and back, wherein the tissue engaging formation (38) is essentially oriented away from the distal tip portion (36) in the operating position, as well as a first fluid channel area (76) open to the surrounding area in the region of the head unit (12), wherein the first fluid channel area (76) is at least open to the surrounding area via at least one channel opening (78) provided in the jaw part (24), when the jaw part (24) is in idle position.

11 Claims, 5 Drawing Sheets

(56) References Cited

U.S. PATENT DOCUMENTS

| | | | |
|---|---|---|---|
| 5,569,299 A * | 10/1996 | Dill | A61B 10/06 600/564 |
| 2001/0044635 A1 | 11/2001 | Niizeki et al. | |
| 2004/0082883 A1 | 4/2004 | Kohno | |
| 2004/0082915 A1 * | 4/2004 | Kadan | A61B 1/00068 604/164.04 |
| 2005/0038317 A1 * | 2/2005 | Ratnakar | A61B 1/00105 600/101 |
| 2006/0084885 A1 * | 4/2006 | Reydel | A61B 10/06 600/564 |
| 2011/0237975 A1 | 9/2011 | Secrest et al. | |

FOREIGN PATENT DOCUMENTS

| | | |
|---|---|---|
| DE | 60 2006 000 798 T2 | 5/2009 |
| DE | 10 2009 010 520 A1 | 9/2010 |
| DE | 102009010520 A1 | 9/2010 |
| EP | 0513471 A2 | 11/1992 |
| EP | 0513471 A3 | 11/1992 |
| EP | 1 743 669 B1 | 1/2007 |
| EP | 2241273 A1 | 10/2010 |

OTHER PUBLICATIONS

Search Report issued in corresponding European Application No. 13 19 7782; dated Mar. 12, 2014, 8 pages; with English translation of relevant passage.

\* cited by examiner

ENDOSCOPIC INSTRUMENT FOR RETROGRADE BIOPSY, IN PARTICULAR SYNOVIAL BIOPSY

CROSS REFERENCE TO RELATED APPLICATION(S)

This application claims priority to German Patent Application No. 10 2012 223 788.7, filed Dec. 19, 2012.

The present invention relates to an endoscopic instrument for retrograde biopsy, in particular synovial biopsy, comprising a head unit with a distal tip portion for penetrating the tissue, a jaw part with a tissue engaging formation for removing the biopsy specimen, wherein the jaw part can be pivoted from an idle position to an operating position in direction of the distal tip portion and back, and wherein the tissue engaging formation is essentially oriented away from the tip portion in the operating position, as well as a first fluid channel area open to the surrounding area in the region of the head unit.

An endoscopic instrument for synovial biopsy is known from DE 10 2009 010 520 A1. This known endoscopic instrument has a pointed head unit for penetrating tissue at its distal end portion, wherein a jaw part can be pivotably positioned. In an idle position, the jaw part is essentially pivoted back into the head unit, so that the head unit acting as a trocar can penetrate the tissue. In order to perform a biopsy, the head unit is inserted into a joint cavity surrounded by synovial fluid. A channel opening is provided in the region of the head unit, which is proximally adjacent to the jaw part at its idle position, via which a fluid channel configured in the endoscopic instrument is open toward the surrounding area. If the head unit is completely inserted into the joint cavity, that is to say, including the region having the channel opening, fluid accumulated in the head unit can flow through the channel opening and egress at the proximal end portion of the endoscopic instrument. The egress of fluid indicates that the channel opening provided at the head unit is positioned inside the joint cavity. The jaw part can then be pivoted from its idle position to the pointed distal end portion of the head unit until it is approximately orthogonal with respect to the head unit. A tissue engaging formation configured at the jaw part, for example a plurality of teeth or the like, is oriented in direction of the distal end portion of the head unit, that is to say, in proximal direction. By withdrawing the endoscopic instrument, that is to say, performing a movement to pull out the head unit from the joint cavity, the jaw part protruding laterally from the jaw part is brought in contact with the interior of the synovial joint, which will be recognized by an increased pull-out resistance. Part of the synovial fluid can be removed as a biopsy specimen by pivoting back the jaw part in direction of its idle position and can be kept in the head unit in the idle position of the jaw part by further withdrawing the endoscopic instrument.

Such an endoscopic instrument allows for the possibility of performing a biopsy, for example a synovial biopsy, without causing substantial damage to the tissue or having to perform major incisions to insert the endoscopic instrument into the tissue or into the region to be examined. Furthermore, the retrograde mode of operation including the indication of the position of the head unit by the egress of fluid allows disregarding any additional optical instruments that show, for example, the exact position of the head unit, by way of example, inside a joint cavity.

It is the object of the present invention to further develop such an endoscopic instrument so that an improved functionality is accomplished when performing a retrograde biopsy.

According to the present invention, this object is attained by an endoscopic instrument for retrograde biopsy, in particular a synovial biopsy, comprising a head unit with a distal tip portion for penetrating the tissue, a jaw part with a tissue engaging formation for removing the biopsy specimen, wherein the jaw part is pivoted from an idle position to an operating position in direction of the distal tip portion and back, and wherein the tissue engaging formation is essentially oriented away from the tip portion in the operating position, as well as a first fluid channel area open toward the surrounding area in the region of the head unit.

It is further provided that the first fluid channel area is at least open toward the surrounding area via at least one channel opening provided in the jaw part when the jaw part is in idle position.

The design length of the head unit, and as a result the longitudinal section of the endoscopic instrument to be inserted, for example, into a joint cavity in order to perform a retrograde biopsy, in particular a synovial biopsy, can be reduced by integrating the channel opening that receives the fluid from or feeds said fluid into the body to be examined, that is, for example, a joint cavity, in the region of the jaw part. This implies a lesser penetration depth into the body to be examined and thus a correspondingly lesser strain on the examined body or also a correspondingly lower risk of causing injuries in the region to be examined.

An actuating unit with an actuating stem carrying the head unit at its distal end portion and a movable actuating organ included in the actuating stem for pivoting the head unit are proposed for the purpose of reliably positioning the head unit in the region to be examined when performing a biopsy and being able to pivot the head unit between its idle position and its operating position.

For the transmission of the actuating force between the actuating organ and the jaw part provided at the head unit it is proposed to provide the head unit with a first head unit preferably detachably mounted on the end portion of the actuating stem and with a second head unit that can be displaced by the actuating organ in a displacement direction relative to the first head unit, wherein the jaw part is coupled in a pivoting manner to the first head unit around a first pivot axis and to the second head unit around a second pivot axis. The pivoting of the jaw part can thus be forced or a displacement movement can be converted into a pivoting motion by generating a relative movement between both head units as a result of the coupling of the jaw part to each of these head units.

In an advantageous arrangement, the actuating force can be reliably generated or transmitted in both actuating directions by ensuring that the actuating organ comprises an actuating rod coupled at its distal end portion to the second head unit for a joint displacement in displacement direction that can be actuated at its proximal end portion by means of a manipulation arrangement.

An impairment of the movement of the head unit by the tissue to be penetrated can be prevented or minimized by configuring a slot for the jaw part in the second head unit which is essentially closed off in the idle position of the jaw part, so that the jaw part is included at least in some sections in this slot or in the perimeter of the second head unit, and thus in the head unit, and can thus be kept countersunk in the head unit.

The distal tip portion can be provided on the second head unit and essentially through or in the distal end portion of the second head unit, and thus also of the endoscopic instrument.

In order to ensure that the fluid is essentially only exchanged via the channel opening provided in the jaw part in the idle position of the jaw part, it is provided that the first fluid channel area is essentially delimited by the first head unit, the second head unit and the jaw part and open toward the surrounding area via the at least one channel opening in the jaw part in the idle position of the jaw part.

It can further be provided that the second head unit is supported or can be supported in displacement direction at the first head unit in the idle position of the jaw part. It can be ensured in this way that the jaw part is firmly supported in displacement direction during the penetration motion and the restoring force acting on the second head unit and that no undefined relative movements take place between the first head unit and the second unit.

In order to connect the first fluid channel area provided in the head unit to other fluid guiding system areas it is proposed to provide the first head unit with a coupling arrangement in a proximal end portion of the head unit for coupling to the actuating stem in a distal end portion of the actuating unit, wherein the first fluid channel area in the coupling arrangement is open toward a second fluid channel area configured in the actuating unit.

In this embodiment, the second fluid channel area can be formed in a simple design at least in some section between an inner surface of the actuating stem and an outer surface of the actuating organ.

In order to allow a fluid exchange with system areas that are outside the body to be examined it is proposed to provide the actuating unit at its proximal end portion with a channel bifurcation area open toward the second fluid channel area for the connection to a fluid source or/and a fluid reservoir.

The egress of fluid from the actuating unit guided through both fluid channel areas as well as the ingress of impurities, in particular to the second fluid channel area, can be prevented in that the actuating unit has a fluid impermeable through-opening at its proximal end portion, which closes off the second fluid channel area for the actuating organ. In this case, the channel bifurcation area or alternatively or additionally also at least part of the through-opening can be provided in a coupling element coupled to the actuating stem at its proximal end portion.

The present invention will be described in detail in the following with reference to the enclosed figures, wherein.

Figure 1:
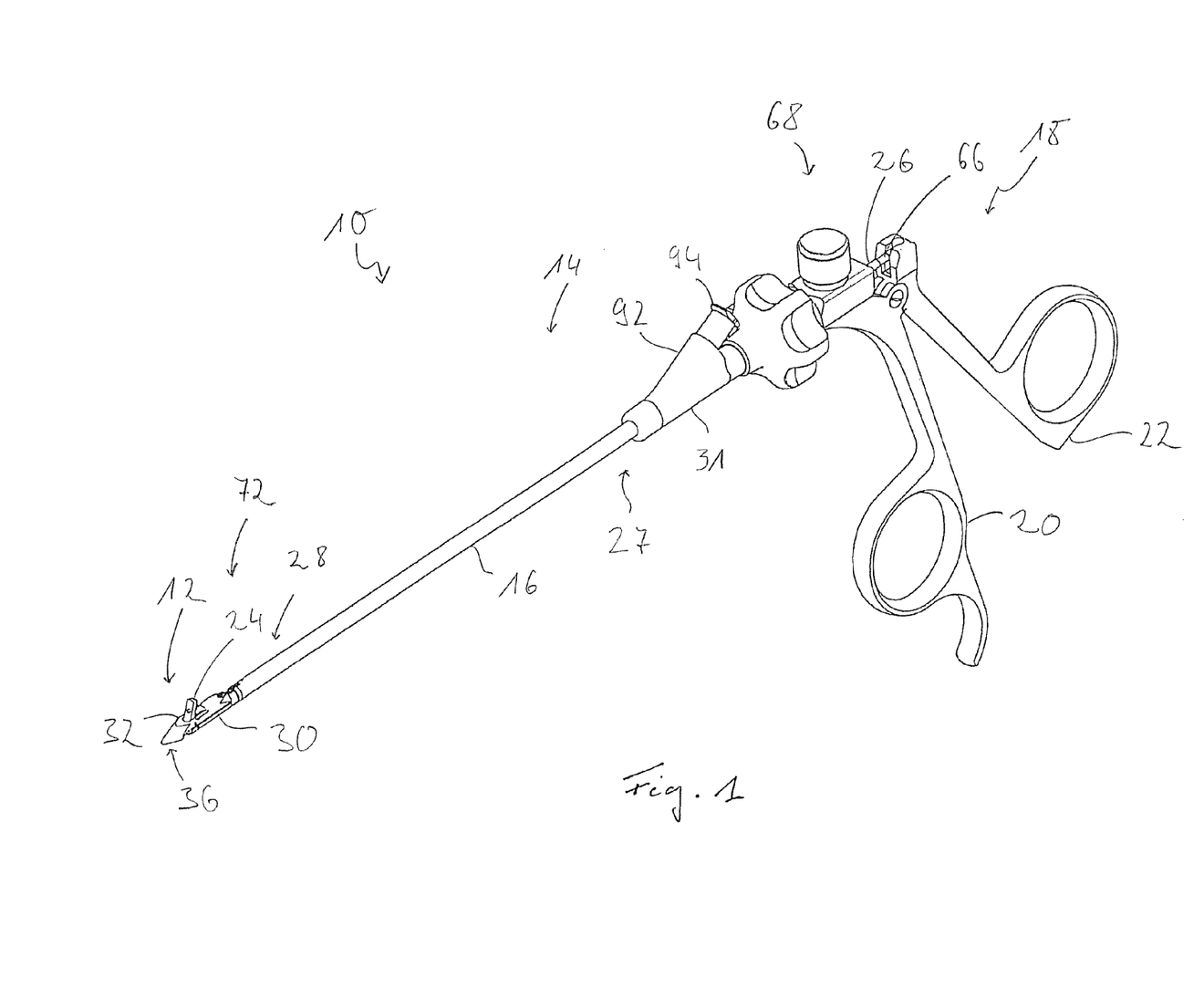
FIG. 1 shows a perspective view of an endoscopic instrument, which can be used, for example, for retrograde biopsy, in particular a synovial biopsy.

FIG. 1 is an endoscopic instrument to be used for retrograde synovial biopsy and identified overall with reference numeral 10. The endoscopic instrument 10 comprises a head unit 12 to be introduced into the region of a body to be examined by means of tissue sampling as well as an actuating unit identified overall with reference numeral 14. The actuating unit 14 comprises a hollow or tubular actuating stem 16 that carries the head unit 12 as well as a manipulation arrangement 20 with two mutually pivoting scissor-like handle parts 20, 22. An actuating force for pivoting a jaw part 24 of the head unit 24 is generated by pivoting both handle parts 20, 22 is transmitted to the head unit 24 via an actuating organ 26, which is configured, for example, as an actuating rod that also penetrates through the actuating stem 16 and which will be described below.

The actuating stem 16 is supported at its proximal end portion 27 on the manipulation arrangement 18 by a coupling element 31. Fluid, for example tissue fluid, can be discharged from or introduced into the region to be examined by means of tissue sampling via the coupling element 31 in the manner that will be described in detail below.

The basic function of the endoscopic instrument 10 of FIG. 1 during a biopsy will be explained in the following with reference to FIGS. 2 to 4.

Figures 2, 3:
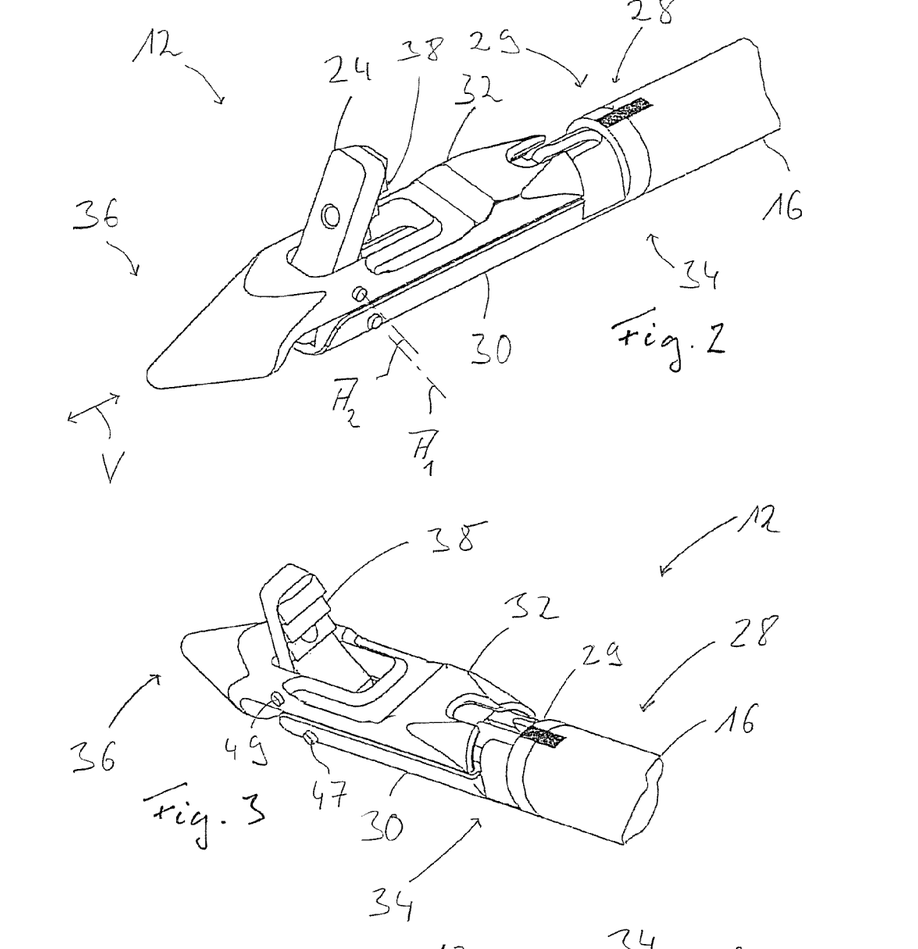
FIG. 2 shows a head unit provided with a jaw part positioned in the operating position at the distal end portion of the instrument of FIG. 1.
FIG. 3 shows another perspective view of the head unit of FIG. 2.

The head unit 12 shown in FIG. 2 at the distal end portion 28 of the actuating stem 16 comprises a first head portion 30, which is and/or can be detachably affixed by means of, for example, a coupling arrangement 29 configured in the manner of a bayonet catch. The head unit 12 further comprises a displaceable second head portion 32 that can be displaced back and forth relative to the first head portion 30 in displacement direction V, which can correspond, for example, to a longitudinal direction of the actuating stem 16. While the proximal end portion 34 of the head unit 12 is provided on the first head portion 30 and can be coupled to the distal end portion 28 of the actuating stem 16, the distal end portion 36 of the head unit 12 is provided on the second head part 32, so that the distal end portion 36 and the proximal end portion 34 of the head unit 12 are also displaced relative to each other in displacement direction V during displacement movements of both head portions 30, 32 relative to each other. The head unit 12 has as pointed configuration at the distal end portion 36, so that it can be guided through the tissue of a body creating a passage for the endoscopic instrument 10.

The jaw part 24 is pivotably coupled to the first head portion 30 around a first pivot axis $A_1$ essentially orthogonally to the displacement direction V. The jaw part 24 is likewise also pivotably coupled to the second head portion 32 around a second pivot axis $A_2$ likewise essentially orthogonally with respect to the displacement direction V, wherein both pivot axes $A_1$ and $A_2$ are preferably parallel and eccentric with respect to each other.

Figure 4:
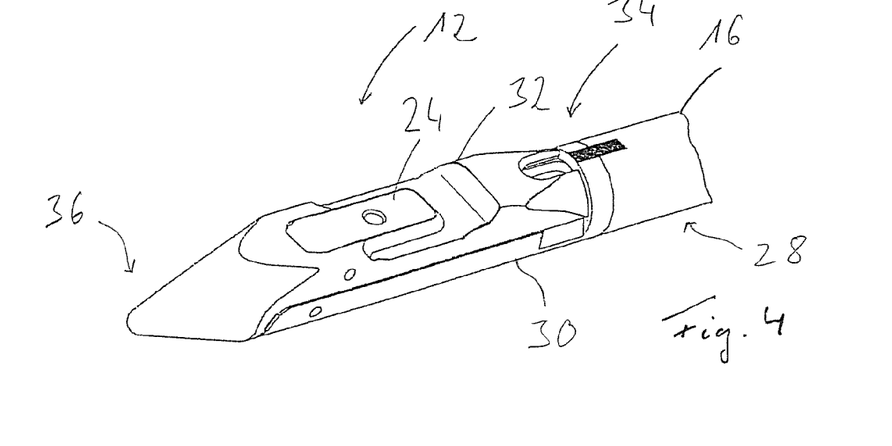
FIG. 4 shows the head unit of the instrument shown in FIG. 1 with a jaw part positioned in an idle position.

When both head portions 30, 32 are displaced relative to each other in the displacement direction V, the head portion 24 is pivoted back and forth between an operating position that can be seen in FIGS. 1 to 3 and an idle position shown in FIG. 4 as a result of the pivotable coupling of the head portion 24 to both head portions 30, 32. When pivoting from the idle position in FIG. 4 to, for example, the operating position visible in FIG. 3, the jaw part 24 pivots in direction of the pointed distal end portion 36 until the jaw part 24 is preferably almost orthogonal to the displacement direction V or also to the longitudinal direction of the actuating stem 16 or also to the head unit 12. In the operating position, a tissue engaging formation 38 provided at the jaw part 24 is oriented away from the direction of the pointed distal end portion 36 and is concealed inside the head unit 12 in the idle position of the jaw part 24 shown in FIG. 4, so that the jaw part can basically be used for cutting backward. It is worth noting that the tissue engaging formation 38 can be configured on the jaw part 24 in the most different ways. It can thus be configured, for example, in the form of a barbed hook punch, as can be seen in particular in FIG. 3. It can also be configured like a spoon with a circumferential barbed hook punch around the border of the spoon and/or as a punch spoon with a mouse tooth.

If the head unit 12 is introduced into the region of the body to be examined, that is, for example, a joint cavity, with the jaw part 24 in an idle position, the jaw part 24 can be pivoted into the operating position by actuating the manipulation arrangement 18 and can then be brought into contact with the tissue to be examined, that is, for example, the inner side of the synovial cavity, by moving the endoscopic instrument 10 out of the body to be examined with its tissue engaging formation 38. When the jaw part 24 is pivoted back away from the distal end portion 36 to its idle position, the jaw part 24 takes tissue as a biopsy specimen with its tissue engaging formation 38 and then keeps it inside the head unit 12 with the jaw part 24 in an idle position, so that the biopsy specimen taken in this way can be guided out of the examined body by withdrawing the endoscopic instrument 10 and can be removed from the head unit 12 or from the jaw part 24 for further examination by again pivoting the jaw part 24 to its operating position outside the body.

Figure 5:
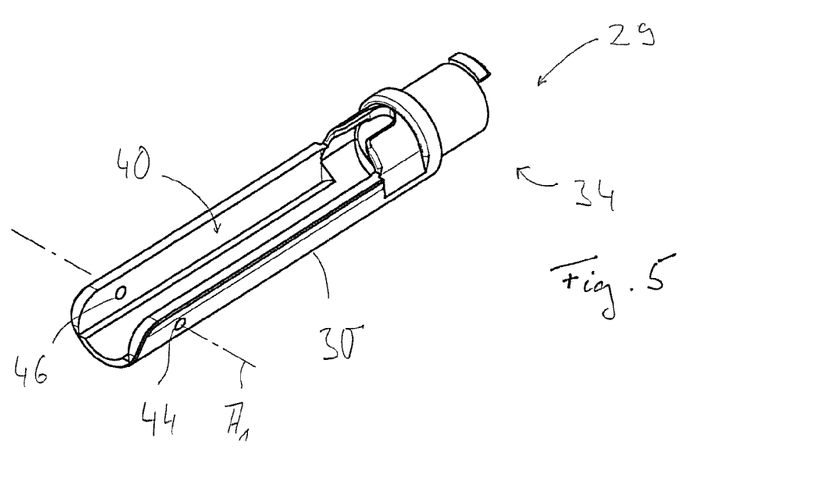
FIG. 5 shows a first head unit of the head unit shown in FIGS. 2 to 4.
Figure 6:
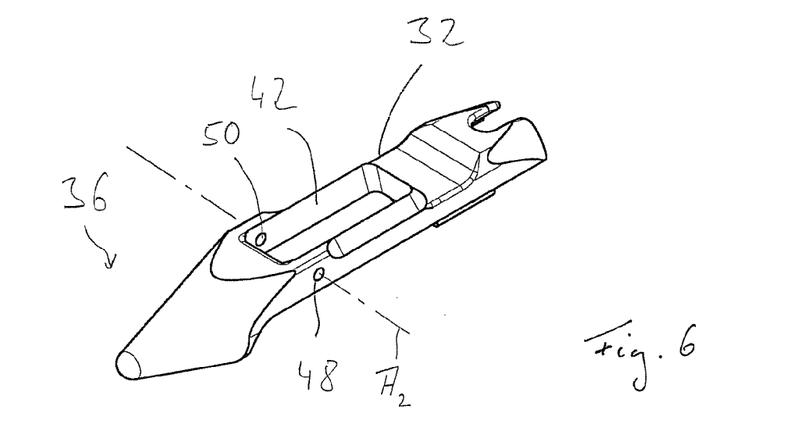
FIG. 6 shows a second head unit of the head unit shown in FIGS. 2 to 4.
Figure 7:
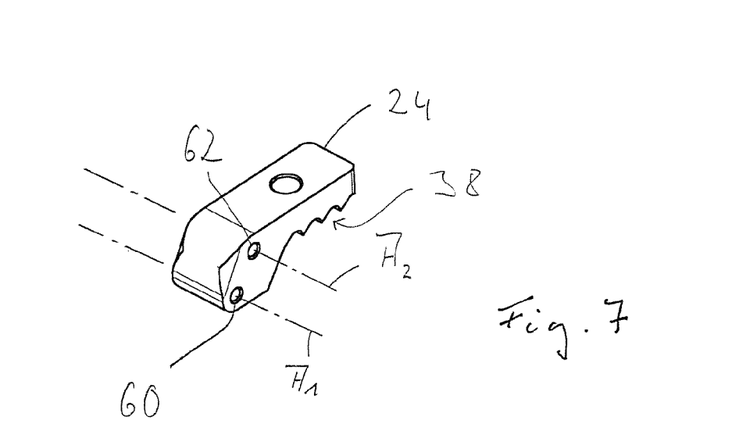
FIG. 7 shows a head unit of the head unit shown in FIGS. 2 to 4.

The components used for the assembly of the head unit 12 are shown in detail in FIGS. 5 to 7. FIG. 5 thus shows a perspective view of the first head portion 30 with its provided coupling arrangement 29, which essentially also provides the proximal end portion 34 of the head unit 12 to be coupled to the actuating stem 16. As already mentioned, the coupling between the first head portion 30 and the actuating stem 16 can be produced in the form of a bayonet catch, so that, on the one hand, a mutually stable mounting of both these components is ensured and, on the other hand, both these components can be easily detached from each other for cleaning purposes.

The first head portion 30 is essentially configured as a tubular or shell-like component that is open in a lateral region and an end portion and provides at least in some sections an inner volume region 40 closed by the second head portion 32, which can be seen in FIG. 6. A slot 42 for holding the jaw part is configured on the second head portion 32 shown in FIG. 6 adjacent to the essentially tapered distal end portion 36 of the head unit 12. When the jaw part 24 is in the idle position, this slot 42 for holding the jaw part is essentially covered or closed by the jaw part 24 shown in FIG. 7, wherein the jaw part 24 is positioned in the idle position relative to the second head portion 24 in such a way that it does not protrude over its outer perimeter (see FIG. 4). This ensures that the penetration of the head unit 12 into a body tissue is not affected by the sections of the jaw part 24 protruding over the outer perimeter of the second head portion 32.

Openings 44, 46 and 48, 50 and 60, 62 disposed in pairs are respectively provided in the first head portion 30, in the second head portion 32, as well as in the jaw part 24. A pivot pin 47 that passes through the openings 44, 46 and 60 can be arranged in such a way that the jaw part 24 can be pivoted around the pivot axis $A_1$ on the first head portion 30 for a pivoted coupling of the jaw part 24 on the first head portion 30. A pivot pin 49 that passes through the openings 48, 50 and 62 can be arranged in such a way that the jaw part 24 can be pivoted around the pivot axis $A_2$ on the second head portion 32 for a pivoted coupling to the second head portion 32. The pivot axes $A_1$ and $A_2$ will also be displaced relative to each other by displacing both head portions 30, 32 relative to each other, so that the displacement of both head portions 30, 32 relative to each other forces the jaw part 24 to pivot between its idle position and its operating position. The second head portion 32 will be slightly deflected laterally in the direction V relative to the first head portion 30 as a result of the fixed distance of both pivot axes $A_1$ and $A_2$ relative to each other over the course of this pivoting motion, which however does not preclude that both these head portions 30, 32 are not essentially displaced relative to each other.

Figure 8:
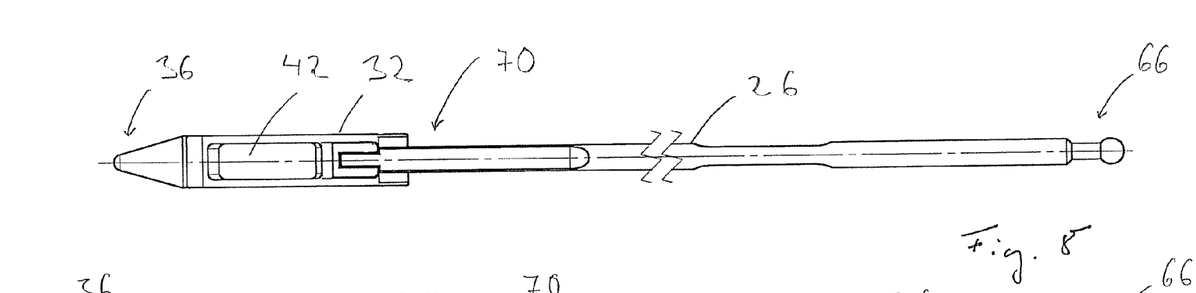
FIG. 8 shows a top view of the second head unit shown in FIG. 6 with the pivotable jaw part attached thereon and an actuating rod coupled to the second head unit.
Figure 9:
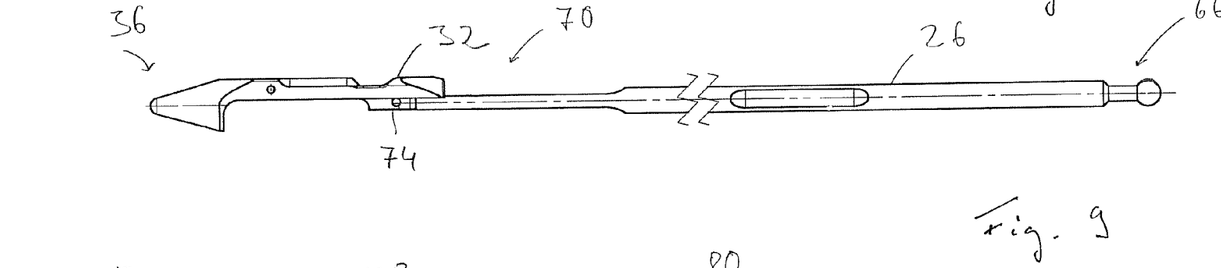
FIG. 9 shows a lateral view of the assembly shown in FIG. 8.
Figure 10:
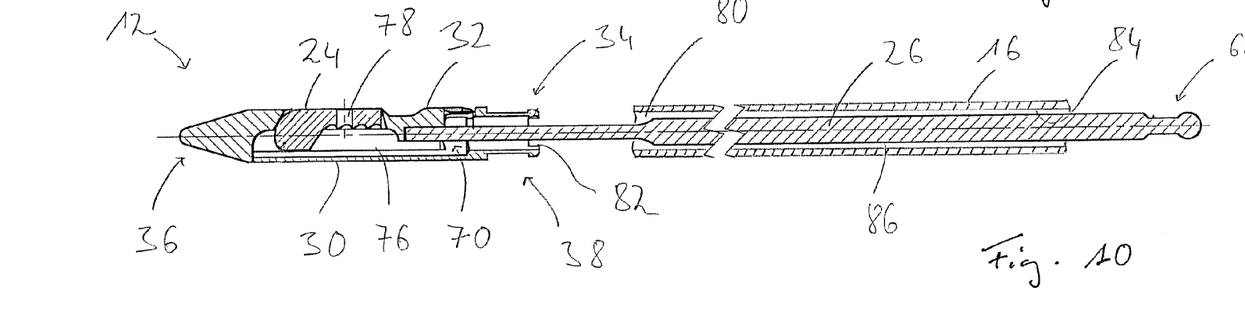
FIG. 10 shows a longitudinal cross section of the head unit shown in FIG. 4 with an actuating rod.

This displacement of both head portions 30, 32 relative to each other is effected by the actuating rod 26 that passes through the actuating stem 16 visible in FIGS. 8 to 10. The actuating rod 26 is coupled at the proximal end 68 of the endoscopic instrument 10 to the manipulation arrangement 18, in particular to the handle part 22, at its proximal end 66, and is coupled at its distal end portion 70 in the distal end portion 72 of the endoscopic instrument 10, for example, by means of a coupling pin 74 to the second head portion 32 for a mutual displacement in displacement direction V. The actuating rod 26 is displaced in distal direction or in proximal direction by pivoting the handle part 22 relative to the handle part 20, depending on the pivoting direction, wherein a displacement of the actuating rod 26 in distal direction produces a corresponding displacement of the second head portion 32 in distal direction and causes the jaw part 24 to be pivoted in direction of the operating position. The displacement of the actuating rod 26 in proximal direction likewise moves the second head portion 32 in proximal direction and thus causes the jaw part 24 to pivot away from the distal end portion 36 of the head unit 12 into its idle position.

Figure 11:
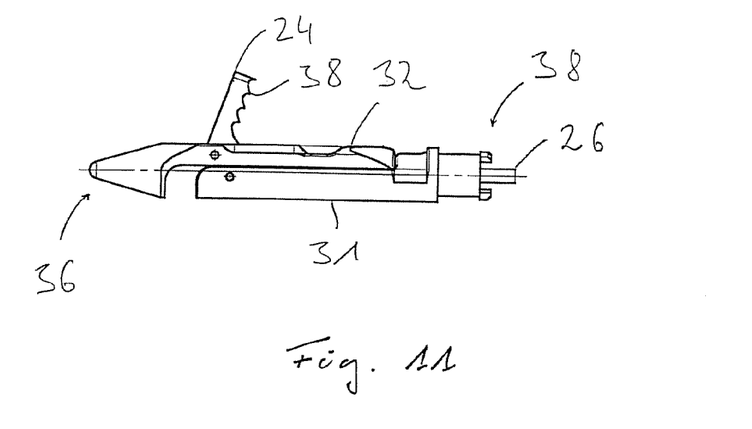
FIG. 11 shows a lateral view of the head unit composed of the parts of FIGS. 5 to 7 with a jaw part positioned in operating position.

A first fluid channel identified overall with reference numeral 76 is configured in the head unit 12 in FIG. 10. The latter is essentially provided by the inner volume area 40 of the first head portion 30 and is enclosed by the first head portion 30 together with the second head portion 32 and also by the jaw part 24, in particular when the jaw part 24 is in its idle position. As is shown in FIG. 10, the second head portion 32 essentially displaced maximally in proximal direction is supported in displacement direction V on the first head portion 30, namely in proximal direction. In this state, the first fluid channel area 76 is open toward the surrounding area in the region of the head unit 12 via a channel opening 78 configured in the jaw part 24. If the jaw part 24 is in its operating position, that is to say, for example, in the state that can also be seen in FIGS. 2, 3 and 11, the first fluid channel 76 is not, or not only, open toward the surrounding area via the channel opening 78 configured in the jaw part 24, but essentially via the entire slot 42 for the jaw part configured in the second head portion 32, or via the volume area 40 of the first head portion 32 which is also open in displacement direction V.

The first fluid channel area 76 is further open toward a second fluid channel area 80 also configured inside the actuating stem 16 at the proximal end 34 of the head unit 12. An essentially axially open opening 82 is especially formed at the proximal end 34 in the first head portion 30, which is open toward the inner volume area of the actuating stem 16. The second fluid channel area 80 is essentially formed between an inner surface 84 of the actuating stem 16 and an outer surface 86 of the actuating rod 26, and is thus configured in this area as a longitudinal annular volume in direction of the actuating stem 16.

Figure 12:
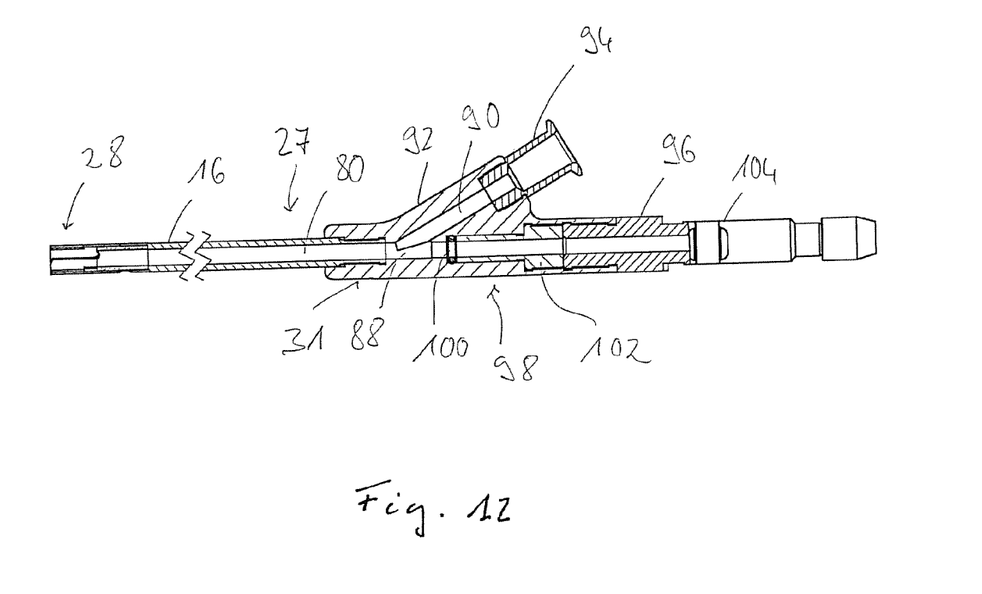
FIG. 12 shows a longitudinal cross section of a part of the actuating unit of the endoscopic instrument of FIG. 1.

The second fluid channel area 80 is continued at the proximal end 27 of the actuating stem 16 by means of a channel-like opening 88 in the coupling element 31, which extends in the longitudinal direction of the actuating stem 16. A channel bifurcation area 90 runs into this channel-like opening 88, wherein the channel bifurcation area is configured in a lateral attachment 92 of the coupling element 31. This lateral attachment 92, or the channel bifurcation area 90 configured therein, can be coupled to a fluid source or fluid reservoir, for example a syringe, via another coupling element 94, for example, a luer coupling element. In this way it is possible to collect or draw tissue fluid from the region to be examined via the first fluid channel area 76 open in the region of the jaw part 24, the second fluid channel region 80 and the channel bifurcation area 90. If such fluid egresses via the channel bifurcation area 90, it is a sign that the head unit 12 and the jaw part 24 provided thereon are positioned in the region to be examined. On the other hand, it will be possible to inject fluid into the region to be examined via the fluid channel areas 76, 80, for example for therapy or local anesthesia.

A fluid-tight through-opening identified overall with reference numeral 98 is formed for the actuating rod 26 in the coupling element 31. It comprises, for example, a sealing element 100 configured as an O-ring. The sealing element 100 is held between a step-like enlargement in the coupling element 31 and an insert 102 inserted therein. The insert 102 is held, in turn, on the coupling element 31 together with a central part 96 in such a way that the actuator rod 26 can be inserted through the coupling element 31, the insert 102 and the middle part 96 up to the region of another insert 104 to be anchored in the manipulation arrangement 18 or can be passed through the latter in such a way that the proximal end 66 can be coupled to the handle 22.

The configuration of an endoscopic instrument described above makes possible the performance of a retrograde biopsy, in particular, for the removal of synovial tissue. The egress of tissue fluid can so be used as an indicator that the region to be examined has been reached. Because this tissue fluid can penetrate into the region of the channel opening configured in the jaw part, an excessively deep penetration with the head unit into the region to be examined, in particular the region of a joint, is not necessary.

Because the endoscopic instrument according to the present invention is composed of different assemblies that can be easily decoupled from each other, in particular the head unit, which can be easily coupled to or decoupled from the actuating stem, the individual assemblies or components of the endoscopic instrument according to the present invention can nevertheless be cleaned and disinfected in a highly reliable manner. It is obvious that the materials used for this purpose for the configuration of the endoscopic instrument ensure an adequate corrosion resistance, as well as an adequate biocompatibility and mechanical strength.

The endoscopic instrument can be provided with a very compact size and thus prevent major damage to the tissue that is penetrated with it. In addition, the fact that the second fluid channel area must not be made available by separate channel elements to be provided for this purpose in the region of the actuating stem, but that the inner volume of the actuating stem can also be used for guiding the fluid is also helpful. This furthermore ensures a reliable fluid flow without substantial fluid flow resistance, but at the same time prevents excessively large dead volumes. A comparatively small amount of joint fluid escaping at the distal end portion can therefore already be detected and used as an indicator of the position in the region to be examined.

The invention claimed is:

1. An instrument for endoscopic retrograde biopsy, comprising:
 a head unit having:
  a distal tip portion configured to penetrate tissue,
  a jaw part with a tissue engaging formation configured to remove a biopsy specimen, wherein the jaw part is adapted to be pivoted from an idle position in a direction of the distal tip portion to an operating position and back, wherein the tissue engaging formation is essentially oriented away from the distal tip portion in the operating position, and
  a first fluid channel area open towards the surrounding area in the region of the head unit when the jaw part is in the idle position, via at least one channel opening provided in the jaw part; and
 an actuating unit having an actuating stem that supports the head unit at its distal end portion and a movable actuating organ incorporated in the actuating stem configured to pivot the jaw part;
 wherein the head unit comprises a first head portion affixed to the distal end portion of the actuating stem and a second head portion adapted to be displaced by the actuating organ in a displacement direction relative to the first head portion, the displacement direction corresponding to a longitudinal direction of the actuating stem, and
 wherein the jaw part is pivotably coupled to the first head portion around a first pivot axis and to the second head portion around a second pivot axis, the first pivot axis and the second pivot axis being essentially orthogonal to the displacement direction.

2. The endoscopic instrument according to claim 1, wherein the actuating organ comprises an actuating rod that is coupled at its distal end portion to the second head unit for a mutual displacement in displacement direction and is configured to be acted upon at its proximal end portion by a manipulation arrangement.

3. The endoscopic instrument according to claim 1, wherein a slot for the jaw part essentially closed off by the jaw part in the idle position is configured in the second head portion or/and that the distal tip portion is provided on the second head portion.

4. The endoscopic instrument according to claim 3, wherein in the idle position of the jaw part, the first fluid channel area is essentially delimited by the first head portion, the second head portion and the jaw part and is open in the jaw part toward the surrounding area via the at least one channel opening.

5. The endoscopic instrument according to claim 1, wherein the second head portion is supported on the first head portion when the jaw part is in the idle position in displacement direction.

6. The endoscopic instrument according to claim 1, wherein the first head portion has a coupling arrangement in the proximal end portion of the head unit, which is to be coupled to the actuating stem in the distal end portion of the actuating unit, wherein the first fluid channel area in the coupling arrangement is open toward a second fluid channel area configured in the actuating unit.

7. The endoscopic instrument according to claim 6, wherein the second fluid channel area is formed at least in some sections between an inner surface of the actuating stem and an outer surfaced of the actuating organ.

8. The endoscopic instrument according to claim 6, wherein the actuating unit has a channel bifurcation area at its proximal end portion that is open toward the second fluid channel area to be coupled to a fluid source or/and a fluid reservoir.

9. The endoscopic instrument according to claim 6, wherein the actuating unit has a fluid-tight through-opening at its proximal end portion that closes off the second fluid channel area for the actuating organ.

10. The endoscopic instrument according to claim 8, wherein the channel bifurcation area or/and at least part of a through-opening is provided in a coupling element coupled to the actuating stem at its proximal end portion.

11. The endoscopic instrument according to claim 1, wherein the first head portion is detachably fixed to the end portion of the actuating stem.

\* \* \* \* \*